(12) United States Patent
Karami (10) Patent No.: US 8,182,458 B2
(45) Date of Patent: May 22, 2012

(54) FASTENER WITH ADHESIVE BLOCKER

(75) Inventor: Hamzeh Karami, Brewster, MA (US)

(73) Assignee: First Quality Products, Inc., Great Neck, NY (US)

( * ) Notice: Subject to any disclaimer, the term of this patent is extended or adjusted under 35 U.S.C. 154(b) by 0 days.

(21) Appl. No.: 11/542,854

(22) Filed: Oct. 4, 2006

(65) Prior Publication Data

US 2008/0086106 A1 Apr. 10, 2008

(51) Int. Cl.
*A61F 13/15* (2006.01)

(52) U.S. Cl. .......................... 604/391; 604/389

(58) Field of Classification Search ........... 604/389–391
See application file for complete search history.

(56) References Cited

U.S. PATENT DOCUMENTS

| | | | |
|---|---|---|---|
| 4,010,753 A | | 3/1977 | Tritsch |
| 4,074,716 A | * | 2/1978 | Schaar .......................... 604/390 |
| 5,019,065 A | * | 5/1991 | Scripps .................... 604/385.21 |
| 5,549,591 A | * | 8/1996 | Landvogt ..................... 604/389 |
| 5,591,521 A | * | 1/1997 | Arakawa et al. ............. 428/352 |
| 5,851,205 A | * | 12/1998 | Hisada et al. ................. 604/390 |
| 5,961,761 A | | 10/1999 | Heindel et al. |
| 6,524,294 B1 | * | 2/2003 | Hilston et al. ................ 604/386 |
| 6,526,631 B1 | * | 3/2003 | Alberg et al. ................... 24/306 |
| 2003/0078558 A1 | | 4/2003 | Karami et al. |
| 2005/0154366 A1 | | 7/2005 | Karami et al. |

FOREIGN PATENT DOCUMENTS

| | | |
|---|---|---|
| EP | 0 974 326 A1 | 1/2000 |
| WO | PCT/US07/80455 | 4/2008 |

OTHER PUBLICATIONS

Supplementary European Search Report and Search Opinion from the European Patent Office corresponding to International Application No. EP 07 84 3855, mailed May 27, 2011.

* cited by examiner

*Primary Examiner* — Lynne Anderson
(74) *Attorney, Agent, or Firm* — Amster, Rothstein & Ebenstein LLP (57) ABSTRACT

An absorbent article including a front waist region having an inner surface, and outer surface, a first lateral end portion and a second lateral end portion, a back waist region having an inner surface, and outer surface, a first lateral end portion and a second lateral end portion, a crotch portion longitudinally connecting the front and back waist regions, and at least one fastener disposed at each of the first and second lateral end portions of the back waist region or the front waist region. The at least one fastener includes a backing layer having a first end portion permanently attached to the back waist region or the front waist region and a second end portion opposite the first end portion, an adhesive layer disposed over at least a portion of the backing layer, a fastening material layer disposed over the adhesive layer at the second end portion of the backing layer, and an outer surface that is free of adhesive to form an adhesive-free region, wherein a fold is formed in the adhesive-free region.

54 Claims, 4 Drawing Sheets

FASTENER WITH ADHESIVE BLOCKER

TECHNICAL FIELD

The present disclosure relates to absorbent articles, and more particularly to pre-fastened absorbent articles have fastening systems that are pre-folded prior to use.

RELATED APPLICATIONS

The present application is related to U.S. Patent Application Publication No. 2003/0078558, U.S. patent application Ser. No. 11/332,645; U.S. Patent Application Publication No. 2006/0095012; U.S. Patent Application Publication No. 2005/0261650; U.S. Patent Application Publication No. 2003/0078558; and U.S. Patent Application Publication No. 2004/0039364, the contents of which are incorporated herein by reference.

BACKGROUND

When manufacturing pre-fastened absorbent articles with associated fasteners, it is desirable to ensure that the positioning of the fasteners on the absorbent article do not interfere with the proper functioning of the absorbent article. For example, in the case of pull-up type absorbent articles having side seals, the fasteners must be disposed on the absorbent article in such a way so as not to block access to the side seals. In the past, this was accomplished by forming a pre-fold in the fasteners before attaching the fasteners to the absorbent article web, which resulted in the free end of the fasteners being spaced laterally inward from the side seals located at the edge of the back and front waist regions of the absorbent article. This added to the complexity of the overall manufacturing process, since extra steps were needed to form the folds in the fasteners, hold the folds in place by securement means and properly position the fasteners on the absorbent article web before adhering the fasteners.

Accordingly, there is a need for an absorbent article requiring a relatively inexpensive and simple manufacturing process that results in proper positioning and configuring of associated fasteners, where the fasteners are easily accessible by the user after tearing of absorbent article side seals.

SUMMARY OF THE INVENTION

An absorbent article according to an exemplary embodiment of the present invention includes a chassis having an inner sheet and an outer sheet. The chassis includes a back waist region having an inner surface, an outer surface, a first lateral end and a second lateral end, a front waist region having an inner surface, an outer surface, a first lateral end and a second lateral end, and a crotch portion longitudinally connecting the back and front waist regions. An absorbent core is disposed over the inner sheet of the chassis at least the crotch portion. At least one fastener is disposed at each of the first and second lateral ends of the back waist region. The at least one fastener includes a backing layer having a first end portion permanently attached to the back waist region and a second end portion opposite the first end portion, an adhesive layer disposed over at least a portion of the backing layer, a fastening material layer disposed over the adhesive layer at the second end portion of the backing layer, and an outer surface at least a portion of which is free of adhesive to form an adhesive-free region, wherein a fold is formed in the adhesive-free region.

An absorbent article according to another exemplary embodiment of the present invention includes a front waist region having an inner surface, and outer surface, a first lateral end portion and a second lateral end portion, a back waist region having an inner surface, and outer surface, a first lateral end portion and a second lateral end portion, a crotch portion longitudinally connecting the front and back waist regions, and at least one fastener disposed at each of the first and second lateral end portions of the back waist region or the front waist region. The at least one fastener includes a backing layer having a first end portion permanently attached to the back waist region or the front waist region and a second end portion opposite the first end portion, an adhesive layer disposed over at least a portion of the backing layer, a fastening material layer disposed over the adhesive layer at the second end portion of the backing layer, and an outer surface, at least a portion of the outer surface being free of adhesive to form an adhesive-free region, wherein a fold is formed in the adhesive-free region.

A method of forming an absorbent article according to an exemplary embodiment of the present invention includes the steps of forming a nonwoven web including a front waist region having an inner surface, an outer surface, a first lateral end portion and a second lateral end portion, a back waist region having an inner surface, an outer surface, a first lateral end portion and a second lateral end portion, and a crotch portion longitudinally connecting the front and back waist regions, stretching the nonwoven web in a machine direction, and attaching at least one fastener to each of the first and second lateral end portions of the front waist region or the back waist region. The at least one fastener includes a backing layer having a first end portion permanently attached to the back waist region or the front waist region and a second end portion opposite the first end portion, an adhesive layer disposed over at least a portion of the backing layer, a fastening material layer disposed over the adhesive layer at the second end portion of the backing layer, and an outer surface, at least a portion of the outer surface being free of adhesive to form an adhesive-free region. The method also includes the step of allowing the nonwoven web to relax to a contracted configuration, whereby a fold is formed in the adhesive-free region of the at least one fastener due to contraction of the nonwoven web.

In at least one embodiment, the adhesive layer is disposed over the entire backing layer, and an adhesive blocking layer is formed over the adhesive layer intermediate the first and second end portions of the backing layer to form the adhesive-free region.

In at least one embodiment, the adhesive layer is disposed over the backing layer only at the first and second end portions to form the adhesive free region intermediate the first and second end portions.

These and other features of this invention are described in, or are apparent from, the following detailed description of various exemplary embodiments of this invention.

BRIEF DESCRIPTION OF THE DRAWINGS

Various exemplary embodiments of this invention will be described in detail, with reference to the following figures, wherein.

DETAILED DESCRIPTION OF PREFERRED EMBODIMENTS

An absorbent article fastener according to various exemplary embodiments of the present invention includes an adhesive blocker that blocks a portion of adhesive applied to the back of the fastener. The adhesive blocker and the portion of the fastener with adhesive provides a variation in the total basis weight and thickness of the fastener, which, as explained in more detail below, results in the production of a fold within the adhesive blocker portion, or an otherwise adhesive-free region, of the fastener during manufacturing of the absorbent article. Thus, the fastener is folded naturally during the manufacturing of the absorbent article, thereby eliminating the need for a separate folding step. Further, in at least one embodiment, the fold formed in the fastener at the adhesive blocker portion prevents the fastener from interfering with side seals formed adjacent to the fasteners. It should be appreciated that, although the fastener according to the present invention is described herein as being used in conjunction with pull-up absorbent articles and conventional briefs, the fastener may also be used in any other type of absorbent article, such as, for example, a T-shaped diaper.

Figure 1:
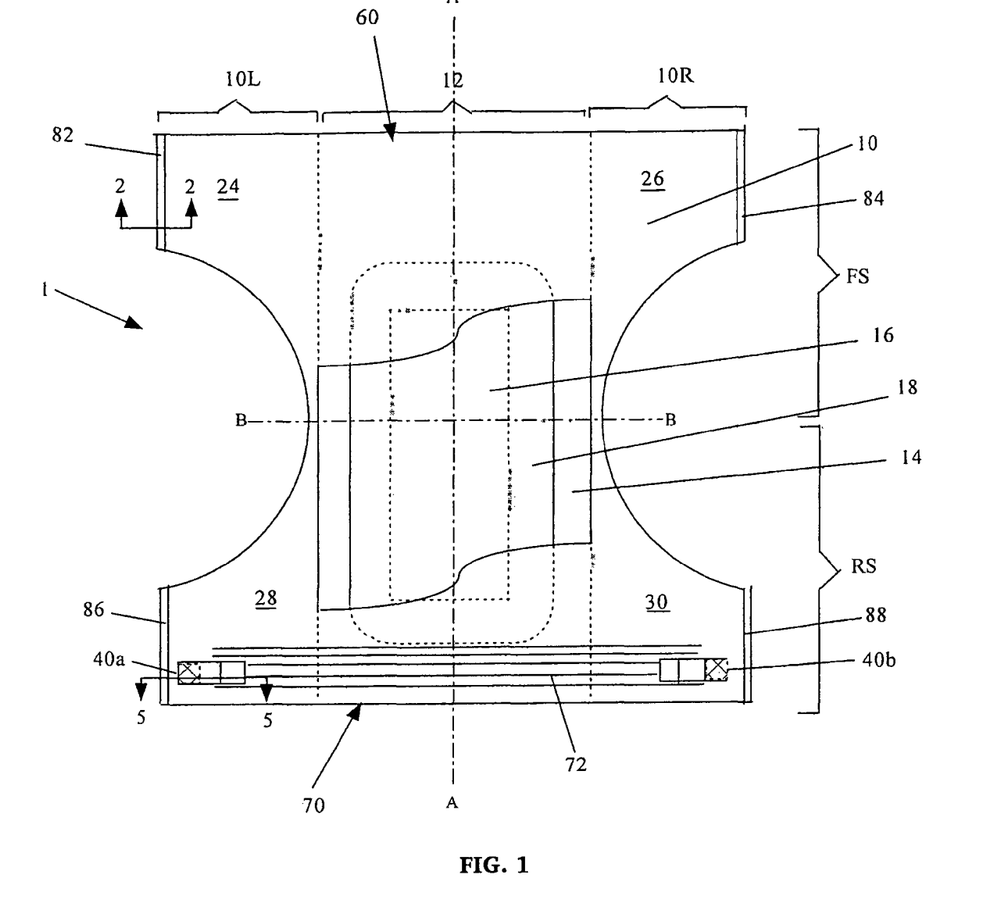
FIG. 1 is a partially cut away plan view of an absorbent article according to an exemplary embodiment of the present invention.

FIG. 1 is a plan view of a pull-up absorbent article, generally designated by reference number 1, that incorporates the fasteners according to an exemplary embodiment of the present invention. The pull-up absorbent article 1 has a longitudinal axis defined by longitudinal centerline A, the term "longitudinal", as used herein, referring to a line, axis or direction in the plane of absorbent article 1 that is generally aligned with, or parallel to, longitudinal centerline A and defines the length of absorbent article 1. Transverse axis B extends through absorbent article 1, intersecting longitudinal centerline A at a right angle in the plane of absorbent article 1, typically at about the midpoint of centerline A. Transverse axis B defines the transverse orientation relative to absorbent article 1 and divides absorbent article 1 into front and rear sections FS and RS respectively. As used herein, the term "transverse" refers to a line, axis or direction that is generally perpendicular to the longitudinal direction and defines the width of absorbent article 1.

The perimeter of absorbent article 1 is defined by outer sheet 10 and inner sheet 20. The absorbent article 1 can be divided into three regions: a containment assembly 12 which extends symmetrically along longitudinal centerline A, and two longitudinally disposed portions 10L and 10R which extend variably in the transverse direction along their length and which define the left and right sides of the absorbent article 1, respectively. In its preferred embodiment, the absorbent article 1 has an "hourglass" configuration wherein portions 10L and 10R narrow to form a crotch region at transverse axis B between front and rear sections FS and RS.

Containment assembly 12 is attached to the inner sheet 20, and includes a topsheet 14, an acquisition layer 16, and an absorbent core 18. Crotch elastic bands and/or wetness indicators (not shown) may be added to one of the components of containment assembly 12. Containment assembly 12 is mounted upon inner sheet 20 to form the absorbent article 1.

Containment assembly 12 is preferably attached to the inner sheet 20 symmetrically along longitudinal centerline A. As containment assembly 12 is necessarily narrower and preferably shorter than at least some portions of inner sheet 20 and outer sheet 10, portions of inner sheet 20 and outer sheet 10 are not overlapped by containment assembly 12. In the preferred embodiment, the hourglass shape formed by outer sheet 10 and inner sheet 20 results in two wings in each of longitudinal portions 10L and 10R where containment assembly 12 is not present. Wings 24 and 26 form part of front waist region 60 of the absorbent article 1, and wings 28 and 30 form part of back waist region 70 of the absorbent article 1. Rear wings 28 and 30 are provided with hook-type fasteners 40a and 40b, respectively. Although there are two hook-type fasteners shown in FIG. 1 with one fastener disposed at each wing 28 and 30, any number and configuration of hook-type fasteners can be used in conjunction with the diaper according to the various exemplary embodiments of the present invention. The structure of the fasteners 40a and 40b are explained in more detail below.

Side seals 82, 84, 86 and 88 are formed at the lateral ends of wings 24, 26, 28 and 30, respectively. The side seals 82, 84, 86 and 88 may be sealed by, for example, ultrasonic heat or adhesive. When a wearer first puts on the pull-up absorbent article 1, the side seal 82 is connected to side seal 86 and side seal 84 is connected to side seal 88. Thus, the lateral end of the wing 24 is connected to the lateral end of the wing 28 and the lateral end of the wing 26 is connected to the lateral end of the wing 30, so that the pull-up absorbent article 1 can be put on similar to conventional underwear. The side seals 82-88 are structured so as to be easily torn apart from one another to determine whether the absorbent article 1 needs to be replaced or when emergency situations require rapid removal of the pull-up absorbent article 1. The absorbent article 1 may be replaced on the wearer without the need for removal of shoes or pants by using the fasteners 40a and 40b, as in a conventional diaper product.

Figure 2:
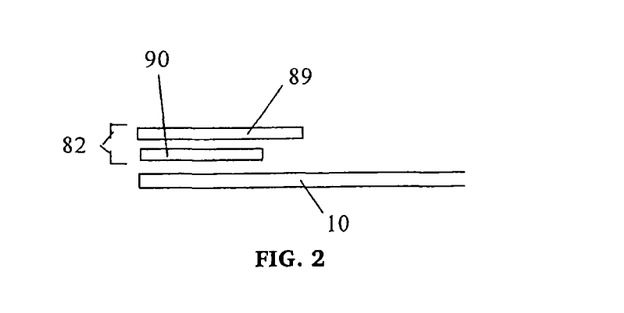
FIG. 2 is a cross-sectional view of the absorbent article taken along line 2-2 in FIG. 1 according to an exemplary embodiment of the present invention.

FIG. 2 is a cross-sectional view of the side seal 82 taken along the line 2-2 in FIG. 1 according to an exemplary embodiment of the present invention. The other side seals 84, 86 and 88 preferably have the same construction as that of the side seal 82, so that descriptions of the side seals 84-88 are omitted. The side seal 82 is made up of the outer sheet 10, the inner sheet 20, and preferably a clean edge inducing material layer, such as nonwoven layer 90, that provides a tearable seam between the frontwaist region 60 and backwaist region 70. The material layer 90 preferably has a basis weight of about 15 gsm to about 100 gsm, and preferably about 25 gsm to about 40 gsm, so as to provide a clean tear edge when the side seal 82 is torn. Alternatively, one of or both the outer sheet 10 and inner sheet 20 may have a basis weight of about 15 gsm to about 30 gsm, so as to provide the clean edge.

Topsheet 14 may be made of any suitable relatively liquid-pervious material currently known in the art or later discovered that permits passage of a liquid therethrough. Examples of suitable inner sheet materials include spun-bonded or carded nonwoven webs of polypropylene, polyethylene, nylon, polyester and blends of these materials, perforated, apertured or reticulated films, and the like. Nonwoven materials are exemplary because such materials readily allow the passage of liquids to the underlying acquisition layer 16, and therethrough to absorbent core 18. The topsheet 14 is preferably formed of a single ply of nonwoven material that may be made of thermally bonded, spunbonded fibers, a spunbond-meltblown-spunbond web, or fibers that have been hydroentangled, having a basis weight of 10-30 grams per square meter and having appropriate strength and softness for use as a topsheet in an application which will be in contact with human skin. Topsheet 14 may be treated with surfactant, rendering it hydrophilic to facilitate the passage of moisture through topsheet 14. The present invention is not intended to be limited to any particular material for top sheet 14 and other top sheet materials will be readily apparent to those skilled in the art.

Acquisition layer 16 may be a single layer or multiple layers made of synthetic or natural material, or a combination of both, or a single multilayer apertured film. Acquisition layer 16 serves to quickly collect and distribute discharged body fluid to absorbent core 18. Because such fluid is typically discharged in gushes, the area of absorbent core 18 proximate to the point of fluid discharge may be overwhelmed by the discharge rate, resulting in a leak. Therefore, the acquisition layer 16 facilitates transport of the fluid from the point of discharge across its surface area to contact other parts of absorbent core 18 into which it can be more readily absorbed. The use of an acquisition layer is well known in the art. Accordingly, acquisition layer 16 of absorbent article 1 may have any well known or as yet undiscovered composition.

Absorbent core 18 may be any absorbent material which is generally compressible, conformable to the shape of the wearer's body and not impeding normal movement by the wearer, and capable of absorbing and retaining liquids such as urine and certain other body exudates. The absorbent core 18 may be manufactured in a wide variety of sizes and shapes, (e.g., rectangular, hourglass, "T"-shaped, asymmetric, etc.) and from a wide variety of liquid-absorbent materials commonly used in disposable diapers and other absorbent articles such as wood pulp fluff. Examples of other suitable absorbent materials include creped cellulose wadding; meltblown polymers; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of absorbent core 18 may also be varied (e.g., the absorbent core may have varying caliper zones, a hydrophilic gradient, an absorbent gelling material gradient, or lower average density and lower average basis weight acquisition zones; or may comprise one or more layers or structures, i.e., members, including sheets or webs.) In addition, each member need not be formed of a single unitary piece of material, but may be formed of a number of smaller strips or components joined together lengthwise or width-wise, as long as they are in fluid communication with one another. The total absorbent capacity of absorbent core 18 should, however, be compatible with the design loading and the intended use of the absorbent article 1. Further, the size and absorbent capacity of the absorbent core 18 may be varied to accommodate wearers ranging from infants through adults.

Outer sheet 10 and inner sheet 20 are made of a liquid and/or vapor-impervious material which may be selected from the same group of materials from which the top sheet 14 was selected and preferably having a basis weight of between 5-45 GSM. Unlike topsheet 14, however, the material used for inner and outer sheets 10, 20 are preferably rendered hydrophobic by omitting the surfactant discussed above with respect to topsheet 14. Inner and outer sheets 10, 20 may be manufactured by well known methods such as thermal bonding, chemical bonding, spun bonding and hydroentanglement. The inner and outer sheets 10, 20 may also be a composite of a film and at least one nonwoven layer attached together by adhesive or heatbonding. The film may be vapor and air permeable but liquid impermeable. The width of the film layer may be narrower than the outer nonwoven layer.

The absorbent article 1 also includes a waist elastic 72 extending transversely across the back waist region 70. As is known in the art, the waist elastic 72 may be composed of strips or cords of elastic material bonded to one of or both the inner and outer sheets 10, 20 to place the inner and outer sheets 10, 20 at the back waist region 70 in a contracted condition, so that the back waist region 70 is able to flex and tighten around the waist of a wearer. Although not shown, the front waist region 60 may also includes a waist elastic.

Figure 3:
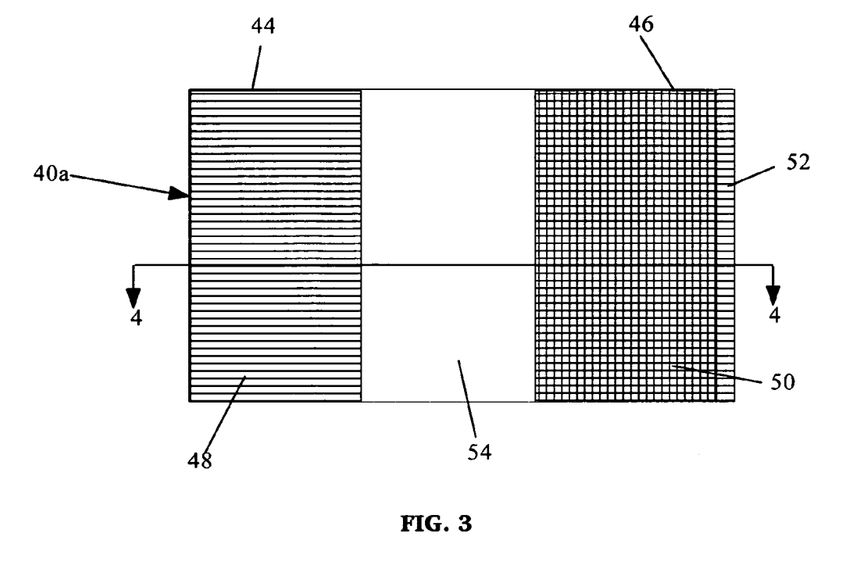
FIG. 3 is a plan view of a fastener according to an exemplary embodiment of the present invention.
Figure 4:
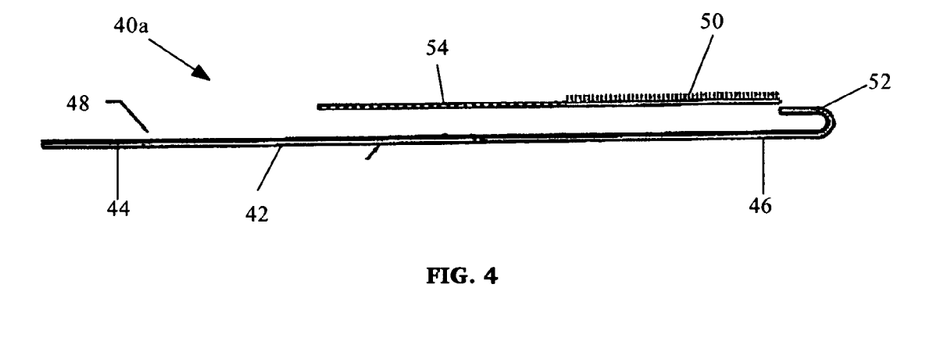
FIG. 4 is a cross-sectional view of the fastener taken along the line 4-4 in FIG. 3 according to an exemplary embodiment of the present invention.

FIG. 3 is a plan view of the fastener 40a and FIG. 4 is a cross-sectional view of the fastener 40a taken along the line 4-4 in FIG. 3 according to an exemplary embodiment of the present invention. The structure of fastener 40a is preferably the same as that of fastener 40b, so that a description of fastener 40b is omitted here. The fastener 40a includes a backing 42 having a first end portion 44 and a second end portion 46. The backing 42 may be, for example, a nonwoven, polymer or textile material. A suitable backing 42 may be tape such as 3M™ Tape 87, available from 3M of St. Paul, Minn. A pressure sensitive adhesive layer 48 is formed over the nonwoven backing 42 from the first end portion 44 to the second end portion 46. A fastening material layer 50 is attached to the nonwoven backing 42 at the second end portion 46 by heat, adhesive or ultrasonic means. The fastening material layer 50 is preferably a strip of hooks, although any other fastening material may be used, such as, for example, adhesive material. The second end portion 46 of the nonwoven backing 42 terminates in a finger-lift portion 52, which may be formed by folding the second end of the nonwoven backing 42 over itself. An adhesive blocking layer 54 is formed immediately adjacent the fastening material layer 50. The adhesive blocking layer 54 is preferably a light-weight nonwoven, having a basis weight of 15 gsm. Alternatively, the adhesive blocking layer 54 may be formed of a thin film layer. The adhesive layer 48 at the first end portion 44 of the nonwoven backing 42 is left exposed for permanent attachment to the back waist region 70 of the absorbent article 1.

During the manufacturing process of the absorbent article 1, the fasteners 40a and 40b are attached to the outer surface of the backwaist region 70 while the backwaist region 70 is held in a stretched configuration. Preferably, the fasteners 40a and 40b are positioned on the backwaist region 70 such that the second ends of the fasteners 40a and 40b are spaced laterally inward from the side seals 86 and 88, respectively, by about 0.5 to 5 inches, depending on the fastener size.

Figure 5:
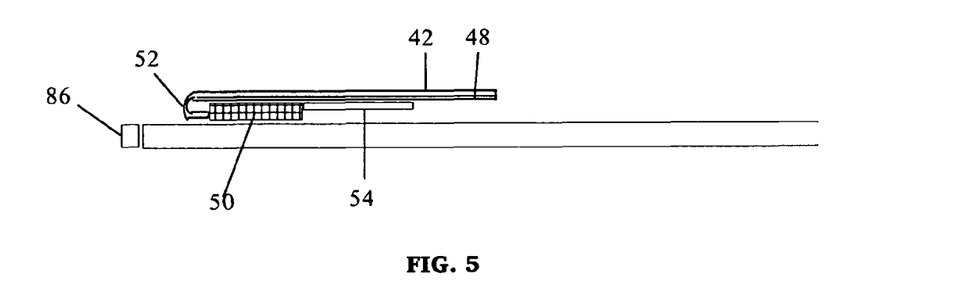
FIG. 5 is a cross-sectional view of the absorbent article in the stretched configuration taken along line 5-5 in FIG. 1 according to an exemplary embodiment of the present invention.
Figure 6:
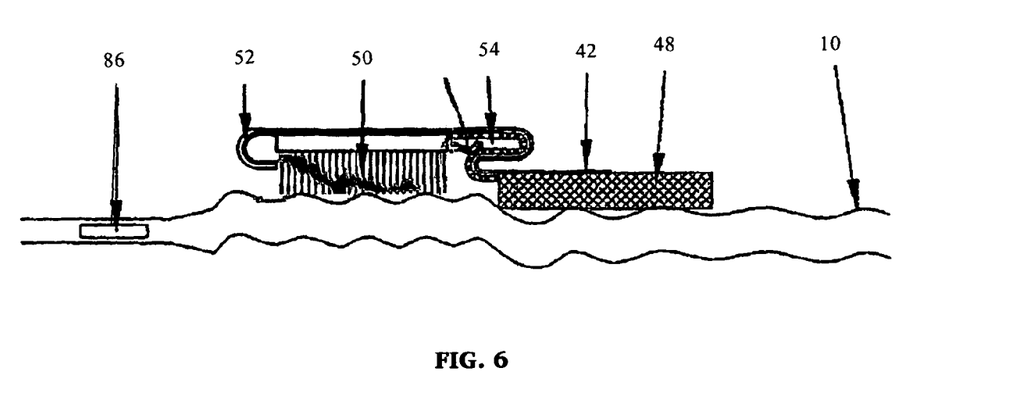
FIG. 6 is a cross-sectional view of the absorbent article in the relaxed configuration taken along line 5-5 in FIG. 1 according to an exemplary embodiment of the present invention.

FIG. 5 is a cross-sectional view taken along the line 5-5 in FIG. 1 of the fastener 40a attached to the backwaist region 70 while still in the stretched configuration, and FIG. 6 is a cross-sectional view taken along the line 5-5 of the fastener 40a attached to the backwaist region 70 after the backwaist region 70 is allowed to relax to a contracted configuration. In particular, as shown in FIG. 6, the contraction of the back waist elastic 72 in the backwaist region 70 results in likewise contraction of the fastener 40a. The strength of contraction of the back waist elastic 72 is preferably stronger than the bending strength of the fastener 40a at the adhesive blocking layer 54, but weaker than the bending strength at the other portions of the fastener 40a. Thus, to accommodate for the contraction of the fastener 40a, a fold forms naturally in the fastener 40a at the adhesive blocking layer 54. For example, a Z-fold may form, including first and second folds 56, 58, or, alternatively, a C-fold may form. Thus, the fasteners 40a and 40b are pre-folded prior to use, and once the side seals 82-88 are torn, the respective fastening material layers 50 of the fasteners 40a and 40b can be disengaged from the backwaist region 70, the fasteners 40a and 40b can be unfolded, and the fastening material layers 50 can be engaged with the frontwaist region 60 to once again secure the absorbent article 1 about the wearer's waist.

Figure 7:
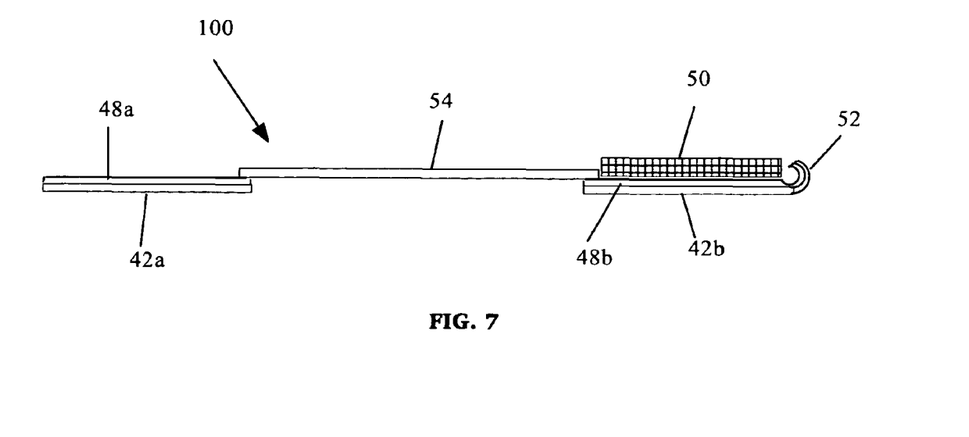
FIG. 7 is a cross-sectional view of a fastener according to another exemplary embodiment of the present invention.

FIG. 7 is a plan view of a fastener, generally designated by reference number 100, according to another exemplary embodiment of the present invention. The fastener 100 is generally the same as the fastener 40a, except for the elimination of portions of the adhesive layer 48 and the backing 42 below the blocking layer 54. Thus, the fastener 100 includes a first backing layer 42a and a second backing layer 42b separated by the blocking layer 54. A first adhesive layer 48a is formed over the first backing layer 42a and a second adhesive layer 48b is formed over the second backing layer 42b. The ends of the blocking layer 54 overlap ends of the first and second adhesive layers 48a, 48b so that the blocking layer 54 is adhered between the first and second backing layers 42a, 42b. This embodiment reduces cost by reducing the amount of backing material required to form the fastener 100. As in the previous embodiment, the relative thinness and low weight of the blocking layer 54 compared to the other portions of the fastener 100 result in the formation of a fold, such as a Z-fold or C-fold, in the blocking layer 54 when the backwaist portion 70 flexes back to a relaxed configuration. The blocking layer 54 may be a nonwoven or film having a basis weight of about 15 gsm to about 50 gsm. Also, the blocking layer 54 may be an elastic film or elastic composite material having about 200 to about 1000% elongation.

Figure 8:
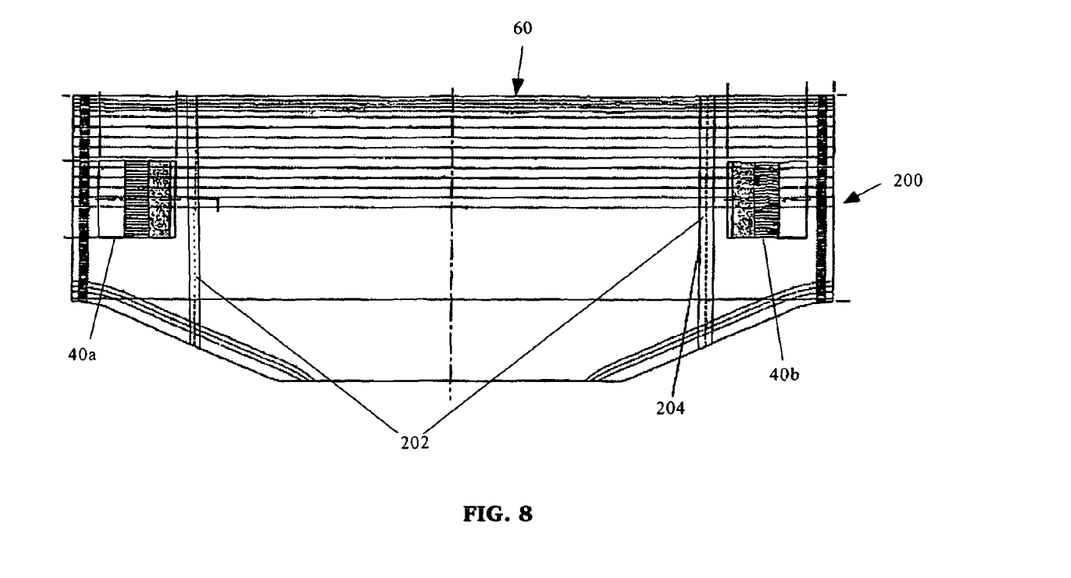
FIG. 8 is a partial plan view of an absorbent article according to another exemplary embodiment of the present invention.

It should be appreciated that the fastener according to the various exemplary embodiments of the present invention may be applied to the frontwaist region 60, rather than the backwaist region 70, of the absorbent article 1. For example, as shown in FIG. 8, which is a partial plan view of an absorbent article according to another exemplary embodiment of the present invention, generally designated by reference number 200, the fasteners 40a and 40b may be applied to the outer surface of the frontwaist region 60. In this embodiment, longitudinally extending perforation lines 202 are preferably formed in the frontwaist region 60 adjacent to the fasteners 40a and 40b. A user may tear along the perforation lines 202 to remove the absorbent article 200, and later refasten the absorbent article 200 using the fasteners 40a and 40b. Reinforcement strips 204 are preferably formed on either side of the perforation lines 202 to ensure that the perforation lines 202 do not prematurely tear during use. The reinforcement strips 203 may be made of materials such as, for example, paper, wet laid nonwoven or any other materials that do not tear easily. Also, prior to formation of the perforation lines 202, heat seal lines having a width of at least ¼ inch may be formed in lines on which the perforation lines 202 are to be formed.

Example 1 below demonstrates the preferred thickness, basis weight and stiffness of the inventive fastener that result in the formation of a fold, preferably a Z-fold, in the fastener when the waist region flexes back to a relaxed configuration.

EXAMPLE 1

The stiffness, basis weight and thickness of various fastener construction samples were measured. In particular, the Gurley Stiffness was determined for each sample. A suitable technique for determining Gurley Stiffness values is set forth in TAPPI Standard Test T 543 om-94 (Stiffness of paper (Gurley type stiffness tester)). A suitable testing apparatus is a Gurley Digital Stiffness Tester: Model 4171-D manufactured by Teledyne Gurley, 514 Fulton Street, Troy, N.Y. 12181-0088. This instrument allows the testing of a wide variety of materials through the use of various lengths and widths in combination with the use of a 5, 25, 50, or 200 gram weight placed in one of three positions on the pointer of the apparatus. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample and are expressed in terms of milligrams. The standard size sample has a width of 1" and a nominal length of 3" (actual length of 3.5"). The actual length of the sample is the nominal length, plus an additional 0.25" of length for holding in the clamp and another 0.25" of length for overlapping the vane. Tables of factors for taking scale readings generated with non-standard sized test samples and converting the readings to the stiffness of the standard size sample are given in the Instruction Manual for the Gurley Stiffness Tester provided by Teledyne Gurley. Accordingly, other designated dimensions for the test sample may also be conveniently employed so long as the appropriate conversion factor is employed to determine the appropriate value which corresponds to the standard size sample.

The fastener constructions were then applied to a composite elastic nonwoven material that resembles an elastic waist region of an absorbent article while the elastic material is in a fully stretched configuration. The elastic material was then allowed to relax to a contracted configuration, and it was observed whether a Z-fold or C-fold formed in the attached fastener construction. The results are shown below in Table 1.

TABLE 1

| SAMPLE NO. | FASTENER CONSTRUCTION | AVERAGE SCALE READING | STIFFNESS (mg) | BASIS WEIGHT OF FASTENER MID-PORTION (gsm) | THICKNESS (in) | FOLD/ FUNCTIONALITY |
|---|---|---|---|---|---|---|
| 1 | 2 Layers 3 M TAPE87 KI6189-CFT00362 Nonwoven Fastening Tape full adhesive coated | 3.38/0.20 | 338.00/19.6 | 214.78 | 0.026 | No/Low Functionality |

TABLE 1-continued

| SAMPLE NO. | FASTENER CONSTRUCTION | AVERAGE SCALE READING | STIFFNESS (mg) | BASIS WEIGHT OF FASTENER MID-PORTION (gsm) | THICKNESS (in) | FOLD/ FUNCTIONALITY |
|---|---|---|---|---|---|---|
| 2 | 3 Layers 3 M TAPE87 KI6189-CFT00362 Nonwoven Fastening Tape full adhesive coated | 3.99/0.16 | 1596.00/65.4 | 322.17 | 0.039 | C-fold/Not Functional |
| 3 | 3 M TAPE87 KI6189-CFT00362 Nonwoven Fastening Tape with 1 Layer 13.5 gsm spunbond nonwoven blocking layer | 0.82/0.12 | 82.00/11.5 | 112.9 | 0.018 | Z-fold/Highly Functional |
| 4 | 3 M KN5053 Nonwoven Fastening Tape zoned area free of adhesive | 1.05/0.07 | 105.00/7.1 | 91.27 | 0.013 | Z-fold/Highly Functional |
| 5 | 1 Layer 3 M TAPE87 KI6189-CFT00362 Nonwoven Fastening Tape full adhesive coated | N/A | N/A | 107.39 | 0.013 | No/Not Functional |

Table 1 shows that good results were obtained with Sample 1 in that the hooks were engaged with the elastic material (thus, somewhat functional even though there was no fold), the best results were obtained with Samples 3 and 4. Thus, the preferred fastener construction has a stiffness within the range of about 82 mg to about 338 mg and a fastener mid-portion basis weight in the range of about 91 gsm to about 214 gsm so that a fold will naturally form in the fastener when the waist region to which it is attached flexes back to a relaxed configuration.

The present invention is intended to encompass a fasteners having a mid-portion having at least an outer surface that is free of adhesive. The mid-portion may be an elastic material, such as an elastic film, elastic nonwoven, or composite elastic nonwoven and elastic film. The adhesive free mid-portion may have any suitable length depending on the overall length of the fastener and size of the absorbent article to which it is attached. For example, the mid-portion may have a length of about 0.5 inches to about 10 inches.

Now that the preferred embodiments have been shown and described in detail, various modifications and improvements thereon will be readily apparent to those skilled in the art. Accordingly, the spirit and scope of the present invention is to be construed broadly and be limited only by the appended claims, and not by the foregoing specification.

What is claimed is:

1. An absorbent article comprising:
a chassis including an inner sheet and an outer sheet, the chassis comprising:
   a back waist region having an inner surface, an outer surface, a first lateral end and a second lateral end;
   a front waist region having an inner surface, an outer surface, a first lateral end and a second lateral end; and
   a crotch portion longitudinally connecting the back and front waist regions;
an absorbent core disposed over the inner sheet of the chassis at least the crotch portion; and
at least one fastener disposed at each of the first and second lateral ends of the back waist region, the at least one fastener comprising:
   a backing layer having a first end portion permanently attached to the back waist region and a second end portion opposite the first end portion;
   an adhesive layer disposed over at least a portion of the backing layer;
   a fastening material layer disposed over the adhesive layer at the second end portion of the backing layer; and
   an outer surface at least a portion of which is free of adhesive to form an adhesive-free region, wherein the fastener has an extended configuration in which the fastening material layer is directly fastened to the back waist region and is not folded over the adhesive-free region and in which the fastening material layer is disposed laterally outwards from the adhesive free region towards a respective one of the first and second lateral ends of the back waist region, and wherein the fastener has a folded configuration in which the entire fastener is folded within the adhesive-free region.

2. The absorbent article of claim 1, wherein the adhesive layer is disposed over the entire backing layer, and an adhesive blocking layer is formed over the adhesive layer intermediate the first and second end portions of the backing layer to form the adhesive-free region.

3. The absorbent article of claim 1, wherein the adhesive layer is disposed over the backing layer only at the first and second end portions to form the adhesive free region intermediate the first and second end portions.

4. The absorbent article of claim 1, wherein the at least one fastener has a basis weight that is less than about 300 gsm.

5. The absorbent article of claim 1, wherein the at least one fastener further comprises a finger-lift portion formed adjacent the fastening material layer at the second end portion of the backing layer.

6. The absorbent article of claim 1, wherein the fastening material layer comprises hooks.

7. The absorbent article of claim 6, wherein the fastening material layer is attached to the backing layer by at least one of heat and ultrasonic welding.

8. The absorbent article of claim 1, further comprising:
a first tearable side seal that connects the first lateral end of the back waist region to the first lateral end of the front waist region; and
a second tearable side seal that connects the second lateral end of the back waist region to the second lateral end of the front waist region, such that the absorbent article is a pull-up type absorbent article.

9. The absorbent article of claim 8, wherein tear strength of the first and second tearable side seals is less than about 2 lbs/in.

10. The absorbent article of claim 8, wherein the at least one fastener is disposed adjacent to and spaced laterally inwards from a corresponding one of the first and second tearable side seals.

11. The absorbent article of claim 10, wherein the second end portion of the at least one fastener terminates at a free end of the at least one fastener, and the free end is spaced from a corresponding one of the first and second tearable side seals by a distance of about 0.2 inches to about 5 inches.

12. The absorbent article of claim 8, wherein at least one of the first and second tearable side seals comprises a strip of material that assists the at least one of the first and second side seals in having a clean edge when the at least one of the first and second side seals is torn.

13. The absorbent article of claim 12, wherein the strip of material is nonwoven or film material.

14. The absorbent article of claim 12, wherein the strip of material has a basis weight of about 20 gsm to about 100 gsm.

15. The absorbent article of claim 1, wherein the at least one fastener has a Gurley Stiffness of about 82 mg to about 336 mg.

16. The absorbent article of claim 1, wherein the back waist region comprises an elastic portion.

17. The absorbent article of claim 16, wherein back waist region has a maximum elongation force of about 1 lb. to about 4 lbs.

18. The absorbent article of claim 1, wherein the at least one fastener is disposed on the outer surface of the back waist region.

19. An absorbent article, comprising:
a front waist region having an inner surface, and outer surface, a first lateral end portion and a second lateral end portion;
a back waist region having an inner surface, and outer surface, a first lateral end portion and a second lateral end portion;
a crotch portion longitudinally connecting the front and back waist regions; and
at least one fastener disposed at each of the first and second lateral end portions of the back waist region or the front waist region, the at least one fastener comprising:
a backing layer having a first end portion permanently attached to the back waist region or the front waist region and a second end portion opposite the first end portion;
an adhesive layer disposed over at least a portion of the backing layer;
a fastening material layer disposed over the adhesive layer at the second end portion of the backing layer; and
an outer surface at least a portion of which is free of adhesive to form an adhesive-free region, wherein the at least one fastener has an extended configuration in which the fastening material layer is directly fastened to the one of the back waist region or the front wait region to which the backing layer is attached and is not folded over the adhesive-free region and in which the fastening material layer is disposed laterally outwards from the adhesive free region towards a respective one of the first and second lateral ends of the one of the back waist region or the front waist region to which the backing layer is not attached, and wherein the fastener has a folded configuration in which the entire fastener is folded within the adhesive-free region.

20. The absorbent article of claim 19, wherein the adhesive layer is disposed over the entire backing layer, and an adhesive blocking layer is formed over the adhesive layer intermediate the first and second end portions of the backing layer to form the adhesive-free region.

21. The absorbent article of claim 19, wherein the adhesive layer is disposed over the backing layer only at the first and second end portions to form the adhesive free region intermediate the first and second end portions.

22. The absorbent article of claim 19, wherein the at least one fastener has a basis weight that is less than about 300 gsm.

23. The absorbent article of claim 19, wherein the at least one fastener further comprises a finger-lift portion formed adjacent the fastening material layer at the second end portion of the backing layer.

24. The absorbent article of claim 19, wherein the fastening material layer comprises hooks.

25. The absorbent article of claim 24, wherein the fastening material layer is attached to the backing layer by at least one of heat and ultrasonic welding.

26. The absorbent article of claim 19, further comprising:
a first tearable side seal that connects the first lateral end portion of the back waist region to the first lateral end portion of the front waist region; and
a second tearable side seal that connects the second lateral end portion of the back waist region to the second lateral end portion of the front waist region, such that the absorbent article is a pull-up type absorbent article.

27. The absorbent article of claim 26, wherein tear strength of the first and second tearable side seals is less than about 2 lbs/in.

28. The absorbent article of claim 26, wherein the at least one fastener is disposed adjacent to and spaced laterally inwards from a corresponding one of the first and second tearable side seals.

29. The absorbent article of claim 28, wherein the second end portion of the at least one fastener terminates at a free end of the at least one fastener, and the free end is spaced from a corresponding one of the first and second tearable side seals by a distance of about 0.2 inches to about 5 inches.

30. The absorbent article of claim 26, wherein at least one of the first and second tearable side seals comprises a strip of material that assists the at least one of the first and second side seals in having a clean edge when the at least one of the first and second side seals is torn.

31. The absorbent article of claim 30, wherein the strip of material is nonwoven or film material.

32. The absorbent article of claim 30, wherein the strip of material has a basis weight of about 20 gsm to about 100 gsm.

33. The absorbent article of claim 19, wherein the at least one fastener has a Gurley Stiffness of about 82 mg to about 336 mg.

34. The absorbent article of claim 19, wherein the front waist region comprises an elastic portion.

35. The absorbent article of claim 34, wherein front waist region has a maximum elongation force of about 1 lb. to about 4 lbs.

36. The absorbent article of claim 19, wherein the at least one fastener is disposed on the outer surface of the back waist region.

37. The absorbent article of claim 19, wherein the at least one fastener is disposed on the outer surface of the front waist region.

38. A method of forming an absorbent article, comprising:
forming a nonwoven web including a front waist region having an inner surface, an outer surface, a first lateral end portion and a second lateral end portion, a back waist region having an inner surface, an outer surface, a first lateral end portion and a second lateral end portion, and a crotch portion longitudinally connecting the front and back waist regions;
stretching the nonwoven web laterally;
attaching at least one fastener to each of the first and second lateral end portions of the front waist region or the back waist region, where the at least one fastener comprises:
a backing layer having a first end portion permanently attached to the back waist region or the front waist region and a second end portion opposite the first end portion;
an adhesive layer disposed over at least a portion of the backing layer;
a fastening material layer disposed over the adhesive layer at the second end portion of the backing layer; and
an outer surface at least a portion of which is free of adhesive to form an adhesive-free region, wherein the fastener has an extended configuration in which the fastening material layer is directly fastened to the back waist region and is not folded over the adhesive-free region and in which the fastening material layer is disposed laterally outwards from the adhesive free region towards a respective one of the first and second lateral ends of the back waist region, and wherein the fastener has a folded configuration in which the entire fastener is folded within the adhesive-free region; and
allowing the nonwoven web to relax to a contracted configuration, whereby a fold is formed in the adhesive-free region of the at least one fastener due to contraction of the nonwoven web.

39. The method of claim 38, wherein the adhesive layer is disposed over the entire backing layer, and an adhesive blocking layer is formed over the adhesive layer intermediate the first and second end portions of the backing layer to form the adhesive-free region.

40. The method of claim 38, wherein the adhesive layer is disposed over the backing layer only at the first and second end portions to form the adhesive free region intermediate the first and second end portions.

41. The method of claim 38, wherein the at least one fastener has a basis weight that is less than about 300 gsm.

42. The method of claim 38, wherein the at least one fastener further comprises a finger-lift portion formed adjacent the fastening material layer at the second end portion of the backing layer.

43. The method of claim 38, wherein the fastening material layer comprises hooks.

44. The method of claim 43, wherein the fastening material layer is attached to the backing layer by at least one of heat and ultrasonic welding.

45. The method of claim 38, further comprising:
forming a first tearable side seal that connects the first lateral end of the back waist region to the first lateral end of the front waist region; and
forming a second tearable side seal that connects the second lateral end of the back waist region to the second lateral end of the front waist region, such that the absorbent article is a pull-up type absorbent article.

46. The method of claim 45, wherein tear strength of the first and second tearable side seals is less than about 2 lbs/in.

47. The method of claim 45, wherein the at least one fastener is disposed adjacent to and spaced laterally inwards from a corresponding one of the first and second tearable side seals.

48. The method of claim 47, wherein the second end portion of the at least one fastener terminates at a free end of the at least one fastener, and the free end is spaced from a corresponding one of the first and second tearable side seals by a distance of about 0.2 inches to about 5 inches.

49. The method of claim 45, wherein at least one of the first and second tearable side seals comprises a strip of material that assists the at least one of the first and second side seals in having a clean edge when the at least one of the first and second side seals is torn.

50. The method of claim 49, wherein the strip of material is nonwoven or film material.

51. The method of claim 49, wherein the strip of material has a basis weight of about 20 gsm to about 100 gsm.

52. The method of claim 38, wherein the at least one fastener has a Gurley Stiffness of about 82 mg to about 336 mg.

53. The method of claim 38, wherein the back waist region comprises an elastic portion, and the step of attaching the at least one fastener comprises attaching the at least one fastener to the outer surface of the back waist region.

54. The method of claim 38, wherein the front waist region comprises an elastic portion, and the step of attaching the at least one fastener comprises attaching the at least one fastener to the outer surface of the front waist region.

* * * * *